United States Patent
Wyrwicz et al.

(10) Patent No.: US 8,452,373 B2
(45) Date of Patent: May 28, 2013

(54) DIFFUSION TENSOR IMAGING-BASED ALZHEIMER'S DIAGNOSIS METHOD

(76) Inventors: Alice M. Wyrwicz, Lake Forest, IL (US); Palamadai N. Venkatasubramanian, Morton Grove, IL (US); Jason C. Pych, Glenview, IL (US)

( * ) Notice: Subject to any disclaimer, the term of this patent is extended or adjusted under 35 U.S.C. 154(b) by 211 days.

(21) Appl. No.: 12/761,397

(22) Filed: Apr. 16, 2010

(65) Prior Publication Data
US 2010/0292560 A1  Nov. 18, 2010

Related U.S. Application Data

(60) Provisional application No. 61/170,099, filed on Apr. 16, 2009.

(51) Int. Cl.
*A61B 5/055* (2006.01)

(52) U.S. Cl.
USPC .......................................................... 600/410

(58) Field of Classification Search
USPC .................. 600/410; 382/128, 131; 128/920, 128/922
See application file for complete search history.

(56) References Cited

PUBLICATIONS

Rose et al Gray and White Matter Changes in Alzheimer's disease A Diffusion Tensor Imaging Study http://onlinelibrary.wiley.com/doi/10.1002/jmri.21231/pdf.*

Mueller et al Diffusion tensor imaging and tractwise fractional ansiotropy statistics:quantitative analysis in white matter pathology, Biomedical Engineering Online http://www.biomedical-engineering-online.com/content/6/1/42.*

* cited by examiner

*Primary Examiner* — Ruth S Smith
(74) *Attorney, Agent, or Firm* — McAndrews, Held & Malloy, Ltd.

(57) ABSTRACT

A system and method is provided in which a diffusion tensor image of the gray matter of a subject's brain is recorded. The diffusion tensor image is used to determine the Fractional Anisotropy of that area of the subject's brain. It has been determined that a decrease in Fractional Anisotropy is related to a decrease in dendritic quality and/or quantity in the subject's brain, which is typically caused by the presence of Alzheimer's Disease. Consequently, the Fractional Anisotropy determination is used to diagnosis the presence of Alzheimer's Disease.

10 Claims, 8 Drawing Sheets

Cognitive Normal

Alzheimer Patient

910

920

930

940

DIFFUSION TENSOR IMAGING-BASED ALZHEIMER'S DIAGNOSIS METHOD

CROSS-REFERENCE TO RELATED APPLICATIONS

The present application claims the benefit of U.S. Provisional Application No. 61/170,099 filed Apr. 16, 2009.

BACKGROUND OF THE INVENTION

The present invention generally relates to a system and method for diagnosing Alzheimer's disease. More specifically, the present invention relates to a system and method for diagnosing Alzheimer's disease using imaging of a live patient.

Fractional anisotropy (FA) is a scalar value between zero and one that describes the degree of anisotropy of a diffusion process. A value of zero means that diffusion is isotropic, i.e. it is unrestricted in all directions. A value of one means that diffusion occurs only along one axis and is fully restricted along all other directions.

FA is a measure that has been used in diffusion imaging where it is thought to reflect fibre density, axonal diameter, and myelination in white matter.

More specifically, FA derived from magnetic resonance diffusion tensor imaging has previously been used solely for characterizing the white matter of the brain. Further, the gray matter of the brain, which includes the hippocampus and cortex, contains dendrites and is structurally different from the white matter. Previously, dendritic quantity has been measured only by histological methods.

BRIEF SUMMARY OF THE INVENTION

It has been determined that the values of FA are positively correlated with the percentage of area occupied by dendrites in the hippocampus. Alzheimer's Disease (AD) and other neurodegenerative diseases are associated with a reduction in dendritic quantity. One or more embodiments disclosed herein may be used for measuring changes in dendritic quantity in the brain of a patient for the diagnosis of AD or in an animal subject used for the development of therapy for AD.

DETAILED DESCRIPTION OF THE INVENTION

Figure 1:
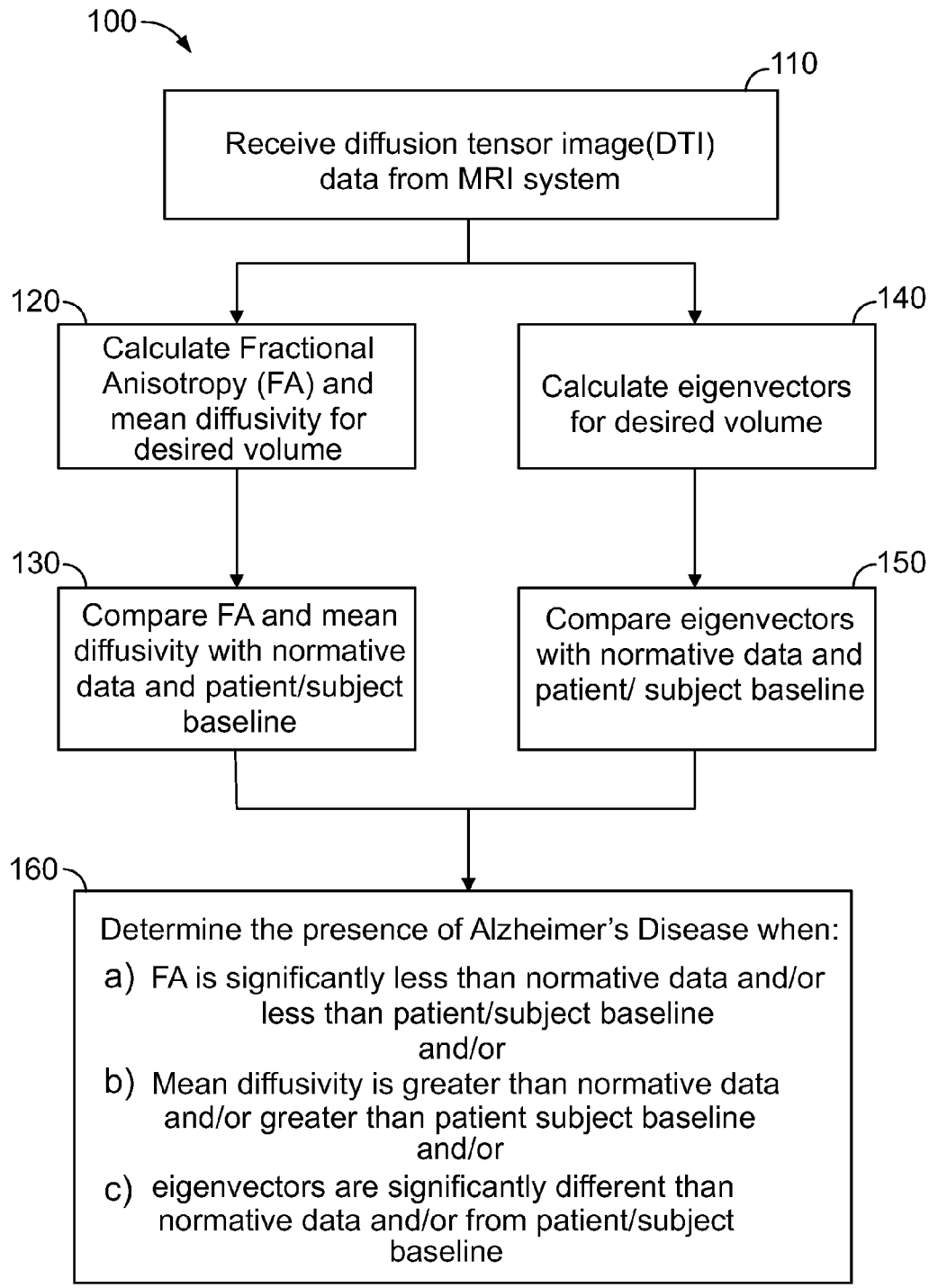
FIG. 1 shows a flowchart of a method for determining the presence of Alzheimer's disease in accordance with one or more embodiments of the present innovation.

FIG. 1 shows a flowchart of a method for determining the presence of Alzheimer's disease in accordance with one or more embodiments of the present innovation. More specifically, in FIG. 1 a magnetic resonance imaging method provides an index (for use as a surrogate measure) for hippocampal dendritic quantity.

The method shown in FIG. 1 uses the measurement of fractional anisotropy (FA) in the hippocampus or (alternatively or in addition) any other gray matter region of animal or human brain preferably using diffusion tensor imaging (DTI). The method shown in FIG. 1 may be used as a diagnostic method or as a bioanalytical method.

FIG. 1 illustrates a flowchart 100 of a method for determining the presence of Alzheimer's Disease (AD) or another neurodegenerative disease or injury. First, at step 110, a desired volume of the brain is imaged, preferably using Magnetic Resonance Diffusion Tensor Imaging (DTI). The volume of the brain that is imaged is preferably the hippocampus and/or the dentate gyrus.

Once the desired volume is imaged, either one or both of the following take place. In a first instance, at step 120, the fractional anisotropy (FA) for the desired volume may be calculated based on the DTI image. Then, at step 130, the FA may be compared with nonnative FA data retrieved from a patient/subject database.

In a second instance, at step 140, the eigenvectors for the desired volume may be calculated based on the DTI image data. Then at step 150, the eigenvalues may be compared with normative eigenvectors from a patient/subject database.

Further, in some embodiments mean diffusivity may be calculated for the desired volume. Alternatively, FA, mean diffusivity and eigenvectors may be calculated and compared. Typically, when FA decreases, mean diffusivity increases.

It has been determined by the present inventors that the values of FA and/or eigenvectors are positively correlated with the percentage of the area occupied by dendrites. Further, it was known that reduced dendritic percentage is correlated with the presence of Alzheimer's Disease. Consequently, one or more embodiments of the present invention provide the ability to use imaging data to estimate dendritic percentage and/or dendritic volume as a diagnostic and evaluative tool in connection with Alzheimer's Disease.

For example, the patient/subject database may include information representing a statistical set of FA and eigenvector values representing a desired patient population. This information may be useful in forming a comparison between the typical dendritic information of healthy individuals and the dendritic information derived from the present FA determination. Alternatively, the subject/patient database may instead include (or may include in addition) dendritic information of individuals previously diagnosed with Alzheimer's Disease which may then be alternatively compared to the FA information or may be compared to the FA information in addition to the comparison of information from healthy individuals.

Additionally, the database may include previous (baseline) results for a specific patient. Baseline may refer to any or all of the previous recorded DTI data for a given patient. Such information may be useful in tracking the progress of Alzheimer's Disease and/or tracking the efficacy of anti-Alzheimer's Disease activity, such as medication for example.

Also, results for a specific patient may be used in combination with multi-patient statistical information.

As one or more examples, as shown in step 160, once the FA and/or eigenvectors have been calculated, the presence of Alzheimer's Disease may be determined when the FA is less than or significantly less than the nonnative data and/or less than the patient's/subject's baseline. Alternatively, the presence of Alzheimer's Disease may be detected when the eigenvectors are different than normative data and/or from the patient's/subject's baseline. Alternatively, Alzheimer's Disease may be detected based on both FA and eigenvector determination. Finally, Alzheimer's Disease may be detected when the mean diffusivity is greater than nonnative data and/or greater than patient subject baseline data.

Further, each of the comparisons identified in step 160 may be employed by itself or in combination with one or more of the other comparisons. Additionally, one or more of the above-identified comparisons may be used to identify and/or track dendritic information in conjunction with a neurodegenerative disease other than Alzheimer's Disease and may also be used with injuries.

Figure 2:
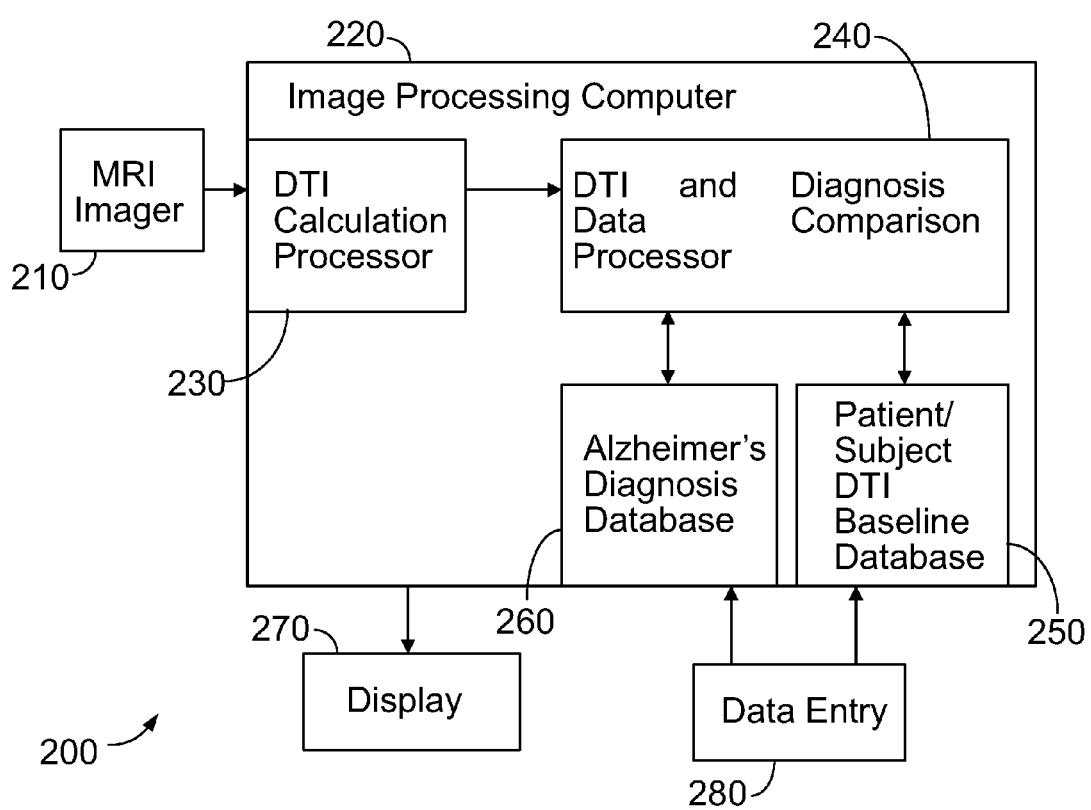
FIG. 2 shows a flowchart of a computational system that may be used in conjunction with one or more embodiments of the present invention.

FIG. 2 illustrates a system 200 for determining the presence of Alzheimer's Disease or another neurodegenerative disease or injury. The system 200 includes a MRI Imager 210, an image processing computer 220, a display 270, and data entry 280. The image processing computer 220 includes a DTI calculation processor 230, a DTI and Diagnosis Data Comparison processor 240, a Patient/Subject database 250, and an Alzheimer's Disease Diagnosis Database 260.

In operation, the system 200 receives an image of a desired volume of the brain from a diffusion tensor image from a MR scan performed by the MRI imager 210. The image is passed to the image processing computer 220. The image processing computer 220 passes the received image data to a Diffusion Tensor Imaging (DTI) calculation processor 230 that determines the eigenvectors and/or FA. The calculated eigenvectors and/or FA are then passed to the DTI Data Comparison and Diagnosis Processor 240.

The DTI Data Comparison and Diagnosis Processor 240 retrieves data from one or both of the Alzheimer's diagnosis database 260 and the patient/subject DTI baseline database 270. The DTI Data Comparison and Diagnosis Processor 240 then compares the calculated eigenvectors and/or FA with the data retrieved from one or both of the Alzheimer's diagnosis database 260 and the patient/subject DTI database 250 in order to determine the presence of an indicator correlated with the presence of Alzheimer's or another neurodegenerative disease or injury as discussed above with regard to FIG. 1.

The display 270 may display the image data of the brain, the data representing the eigenvectors or FA calculation, data from the Alzheimer's diagnosis database 260 and/or data from the patient/subject baseline database 250. Additionally, the display preferably displays the results of the DTI Data Comparison and Diagnosis Processor's determination with regard to the presence or absence (or the likelihood of presence or absence) of Alzheimer's disease or another neurodegenerative disease or injury.

More generally, diffusion tensor imaging (DTI) is an MR imaging technique used to study the existence of ordered structures in tissue. DTI may also be known as diffusion weighted imaging. Motion of water molecules within organized tissues structures is restricted in certain directions by the boundaries of the tissue microstructure. Water diffusion in such restricted environment is highly direction-oriented and is termed anisotropic. Fractional anisotropy (FA) is a measure of diffusion anisotropy which is calculated from diffusion tensor images.

Figure 3:
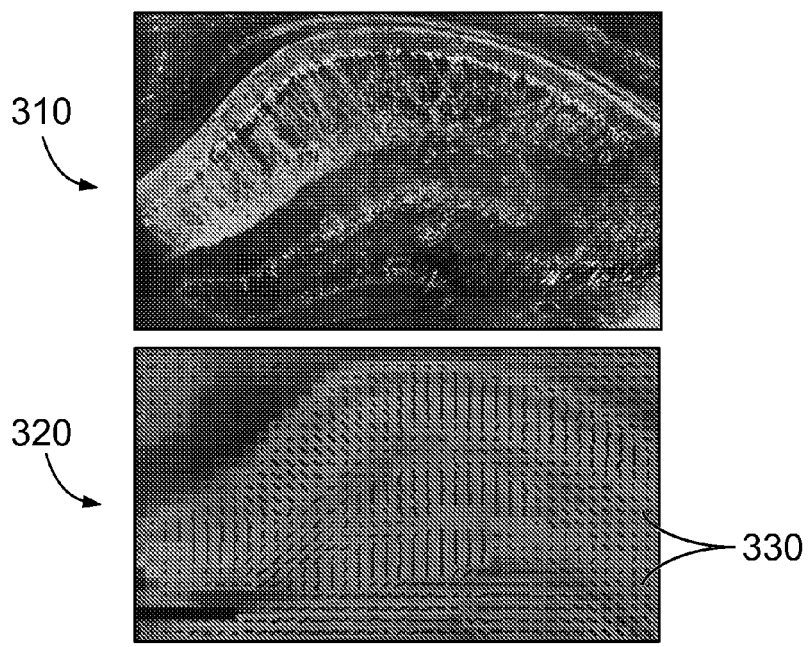
FIG. 3 shows dendrite orientation in the murine hippocampus and dentate gyrus.

FIG. 3 shows dendrite orientation in the murine hippocampus and dentate gyrus. In each subfield of the hippocampus the cell bodies of the principal neurons are arranged in discrete layers. The dendrites of principal neurons radiate into neuropil layers in which the incoming fibers terminate. In FIG. 3, the top image 310 shows the histology of the region. The bottom image 320 is a MR image with overlaid diffusion directionality plot vectors 330 in 2D, and a scale bar with a 500 micrometer scale.

The inventors have verified that anisotropy in the hippocampus arises from this pattern of cellular architecture using morphometric analysis. Based on the experimental verification of the relationship between hippocampal fractional anisotropy and morphometric dendritic quantity in dentate gyrus and CA1 and CA3 subfields of the hippocampus, one or more embodiments of the present invention use the quantitative measure of FA as an index for dendritic quantity in hippocampal subfields. The inventors have also verified experimentally that the density of other cellular components, namely, myelinated axons, soma and blood vessels, is not correlated to anisotropy in the dendritic fields of the hippocampus measured by diffusion tensor imaging.

One or more embodiments disclosed herein may be used for the measurement of dendritic quantity in the hippocampus of animal subjects or humans in normal physiology or in diseased state including but not limited to Alzheimer's disease. Some embodiments of this invention allow for the measurement of dendritic quantity in any gray matter region of the brain. Some embodiments of this invention allow for the measurement of neurogenesis in animals or in humans. In some embodiments of this invention, the term Fractional Anisotropy may be replaced by either Relative Anisotropy (RA), or Trace, or mean diffusivity, or parallel diffusivity or axial diffusivity. Embodiments of this invention may use different graphical representations for diffusion anisotropy including but not limited to color coded directionality representations, whisker plot, cylinder plot, or diffusion ellipsoids.

As mentioned above, only histological approaches are currently available to measure dendritic quantity and arborization. Golgi staining and Sholl analysis are used to quantify dendritic arborization. Unlike MR-based diffusion tensor imaging, histological methods require slicing of the tissue and therefore are not suitable for human studies or for longitudinal animal studies.

Conversely, MR imaging is a non-invasive method that is suitable for in vivo imaging. DTI is magnetic field independent and therefore the present method may be used to measure dendritic quantity not only in mice but also in humans using clinical imagers at a lower field strength, such as 1.5 T and 3.0 T. Unlike histological methods, MR imaging may be repeated on the same subject for longitudinal measurements.

The inventors have investigated the relationship between dorsal hippocampal FA and dendritic density in WT2576 mice (wildtype controls for APP-mutant Tg2576 mice) at 3 and 5 months of age. Hippocampal subfield FA was first measured using DTI.

Figure 4:
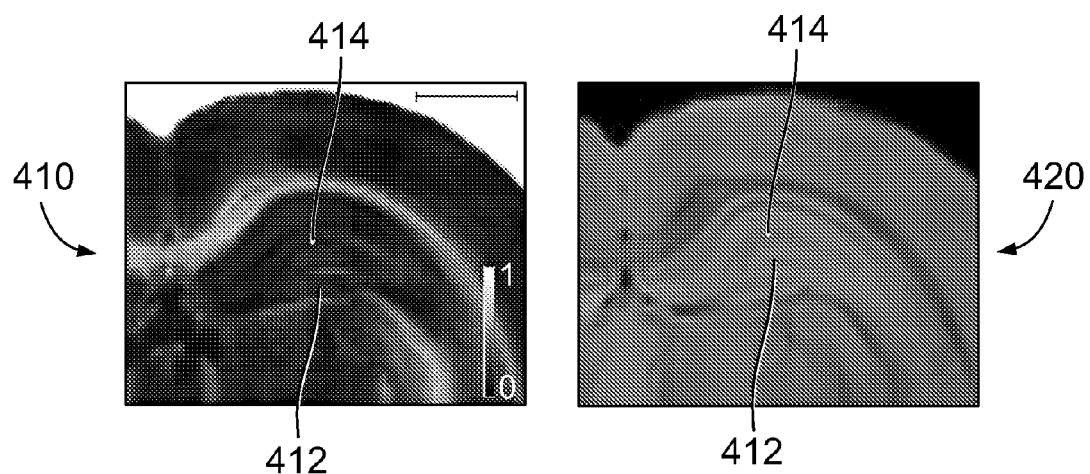
FIG. 4 shows Fractional Anisotropy and trace-weighted maps of the murine brain derived from Diffusion Tensor MR images.

FIG. 4 shows Fractional Anisotropy and trace-weighted maps of the murine brain derived from Diffusion Tensor MR images. The FA map 410 is shown at the left and the trace-weighted map 420 is shown at the right. The different subfield layers (for example, 412, 414) of the dentate gyrus and hippocampus can be distinguished based on their fractional anisotropy values (left). A value of 0 indicates completely isotropic diffusion; a value of 1 indicates highly anisotropic diffusion. The trace-weighted image is used to delineate hippocampal subfields.

After measuring the hippocampal subfield FA using DTI, the proportion of hippocampal volume occupied by dendrites and other tissue components was measured on the same brain samples using a stereologically-correct point-count technique.

Figure 5:
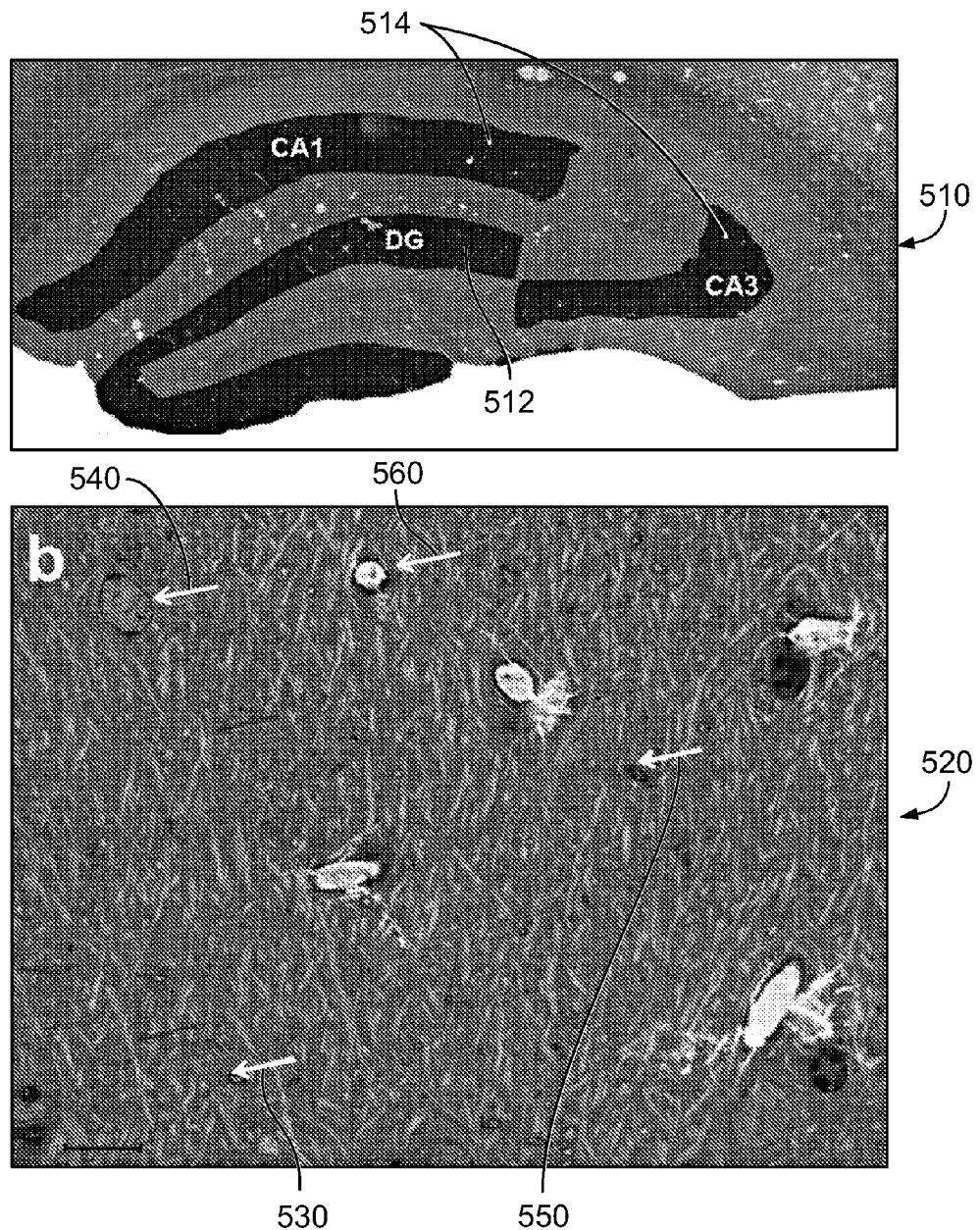
FIG. 5 shows stereology of hippocampal subfields and dentate gyrus in a mouse brain used to quantify dendrites, myelinated axons, soma and blood vessels.

In this regard, FIG. 5 shows stereology of hippocampal subfields and dentate gyrus in a mouse brain used to quantify dendrites, myelinated axons, soma and blood vessels. FIG. 5 includes a top view 510 which shows a 1 μm thick histology section stained with methylene blue/azure II. In the top view 510, the dentate gyrus 512, and hippocampal subfields CA1 and CA3 514 are highlighted.

Figure 6:
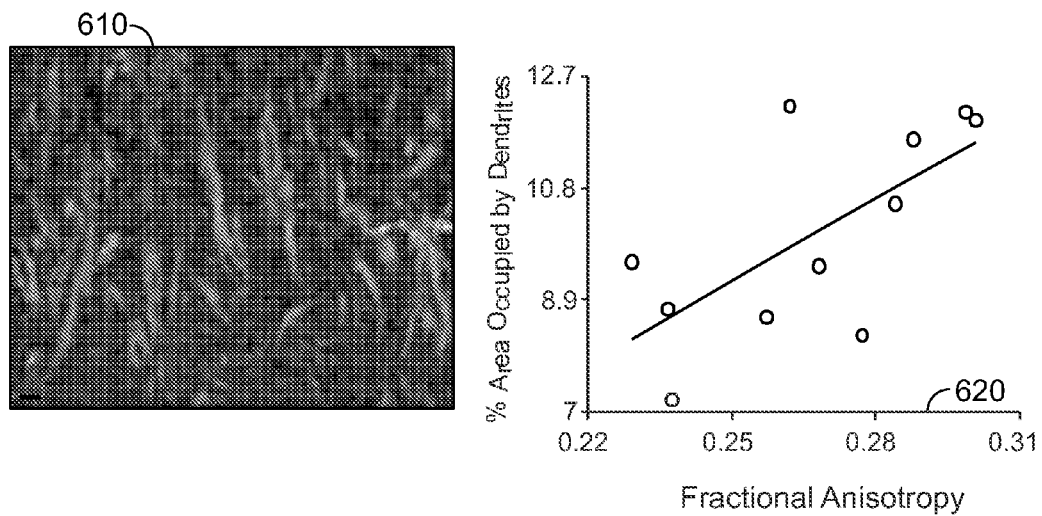
FIG. 6 shows the correlation of FA and percent volume occupied by dendrites in the dentate gyrus of normal control mice.

The bottom view 520 of FIG. 5 shows the dentate gyrus molecular layer sampled at 100×. The bottom view 520 includes areas occupied by dendrites 530, myelinated axons 540, blood vessels 550, and soma 560. The scale bar is 10 μm, In operation, the percentages of area occupied by dendrites, myelinated axons, blood vessels, and soma were quantified using unbiased stereology. The results indicate that dendritic density was positively correlated with FA in dentate gyrus ($p<0.05$); no other tissue component correlated significantly with FA FIG. 6 shows the correlation of FA and percent volume occupied by dendrites in the dentate gyrus of normal control mice. More specifically, FIG. 6 includes a tissue view 610 and a correlation chart 620. The scale bar for the tissue view is 1 μm. As shown in the correlation chart 620, dendritic density is significantly correlated with fractional anisotropy in the dentate gyms ($R^2=0.457$). As shown in the correlation chart, lower FA is correlated with lower percentage area occupied by dendrites and higher FA is correlated with a higher percentage area occupied by dendrites, and vice versa. The percent of volume occupied by blood vessels, soma, and myelinated axons are not significantly correlated with fractional anisotropy.

The significant correlation between FA and dendritic density and a lack of a significant correlation between FA and any other tissue component measured suggest that FA values in dentate gyrus are largely defined by dendritic density. Analysis of the percent of area occupied by dendrites in areas CA1 and CA3 subfields of the hippocampus shows similar dependence. Together, these data verify that FA is a valid surrogate marker for dendritic density in hippocampal subfields.

Figure 7:
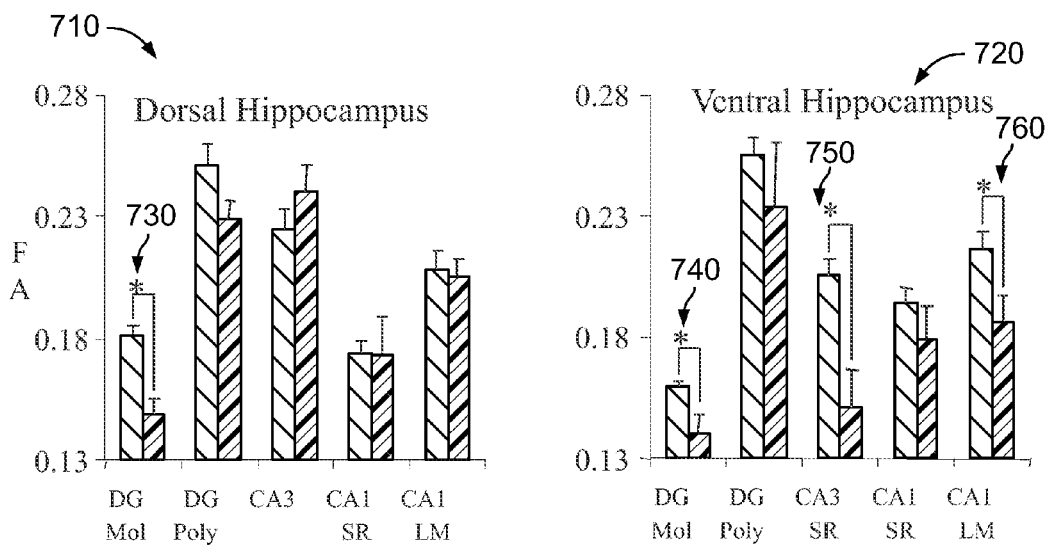
FIG. 7 shows plots comparing FA in the hippocampal regions of APP transgenic and wildtype control mice.

FIG. 7 shows plots comparing FA in the hippocampal regions of APP transgenic and wildtype control mice. FIG. 7 includes a first chart 710 showing the dorsal hippocampus and a second chart 720 showing the ventral hippocampus. FIG. 7 represents an example of the use of FA as a marker for dendritic density in the hippocampal region of the murine brain based on our experimental results.

As can be seen, fractional anisotropy is reduced in 3 month old Tg2576 APP transgenic mice, a model for Alzhiemer's disease, in the following regions: dentate gyrus molecular layer of the dorsal hippocampus 730 and dentate gyrus molecular layer 740, CA3 stratum radiatum (SR) 750 and CA1 lacunosum moleculare (LM) of the ventral hippocampus 760 (* indicates statistically significant differences; $p<0.05$).

Tg2576 mice develop cognitive decline and amyloid plaques, hallmarks of AD-like pathology, only after 8-9 months of age. Thus the reduction in FA, which is a marker for dendritic density, may be used as a predictor of AD-like pathology to follow. In a hypothetical situation in which Tg2576 mice are treated with therapeutic agents, recovery of FA would be indicative of recovery from AD-like pathology. Such a methodology may be expanded to all mammals and humans. The initial measurement and changes in FA may be followed by diffusion tensor imaging. In this application, one or more embodiments of the present invention have the potential to be used as a bioanalytical tool for quantifying dendritic density.

Figure 8:
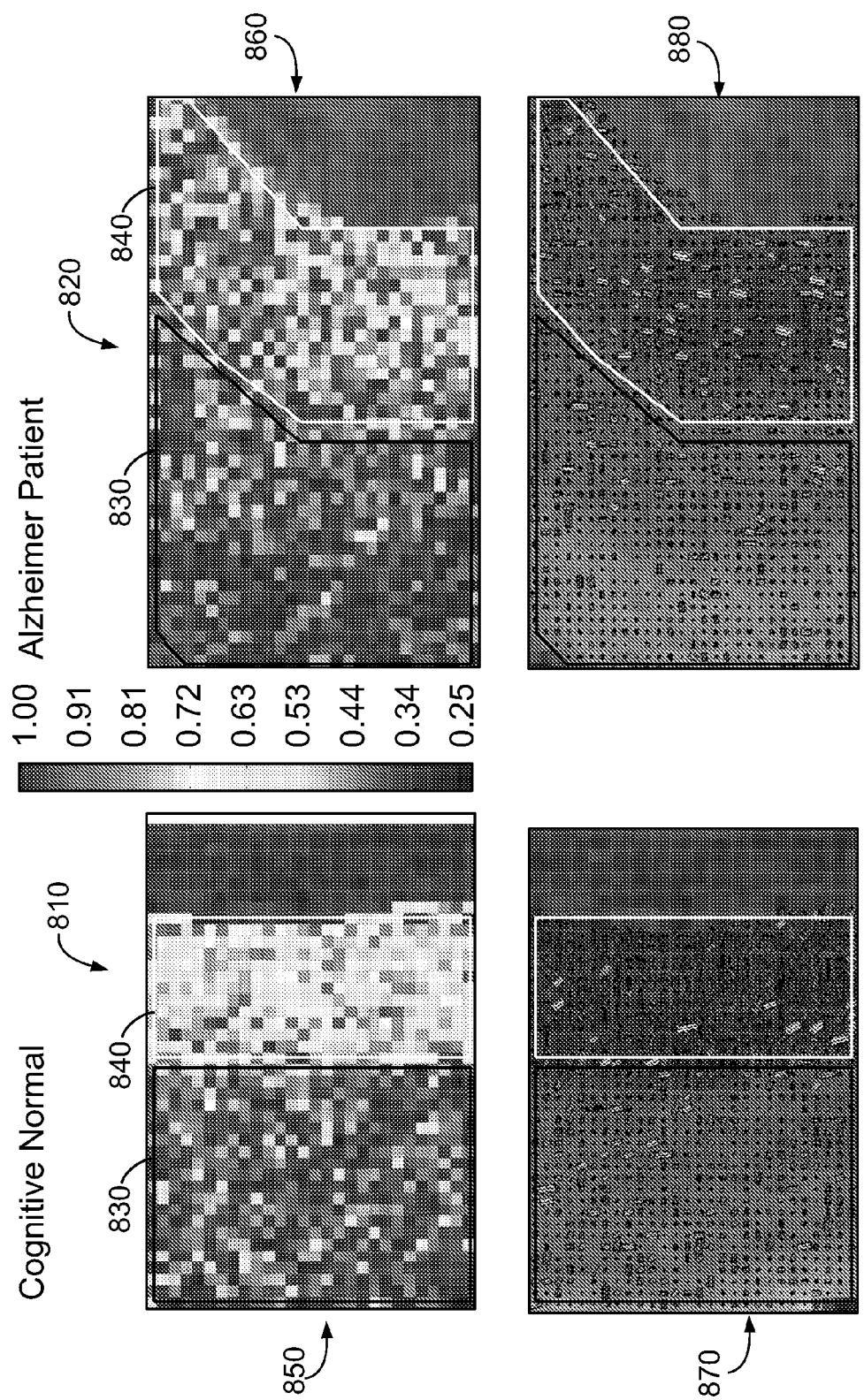
FIG. 8 shows DTI parametric maps of human brain tissue.
Figure 9:
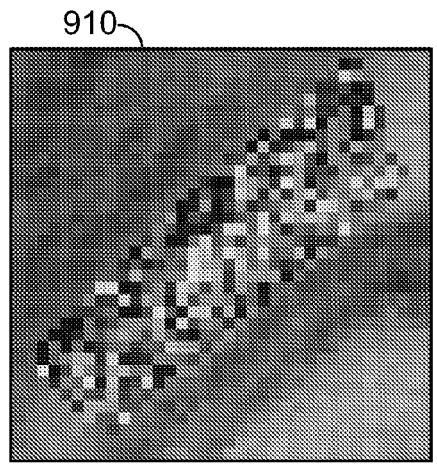
FIG. 9 illustrates FA maps of hippocampal CA1 for both a cognitive normal subject and an AD subject.
Figure 9:
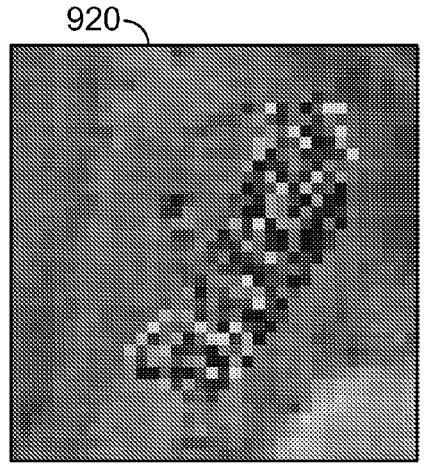
Figure 9:
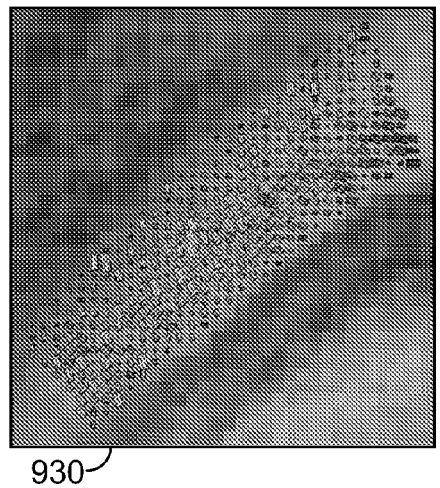
Figure 9:
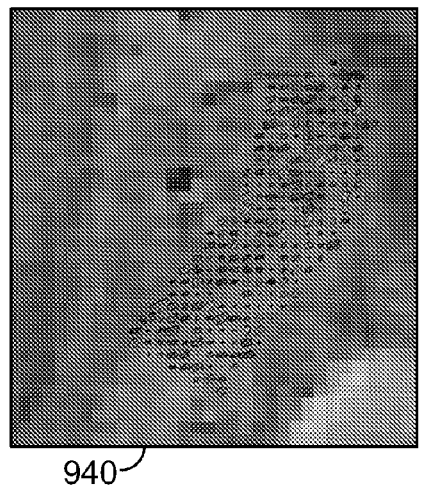
Figure 10:
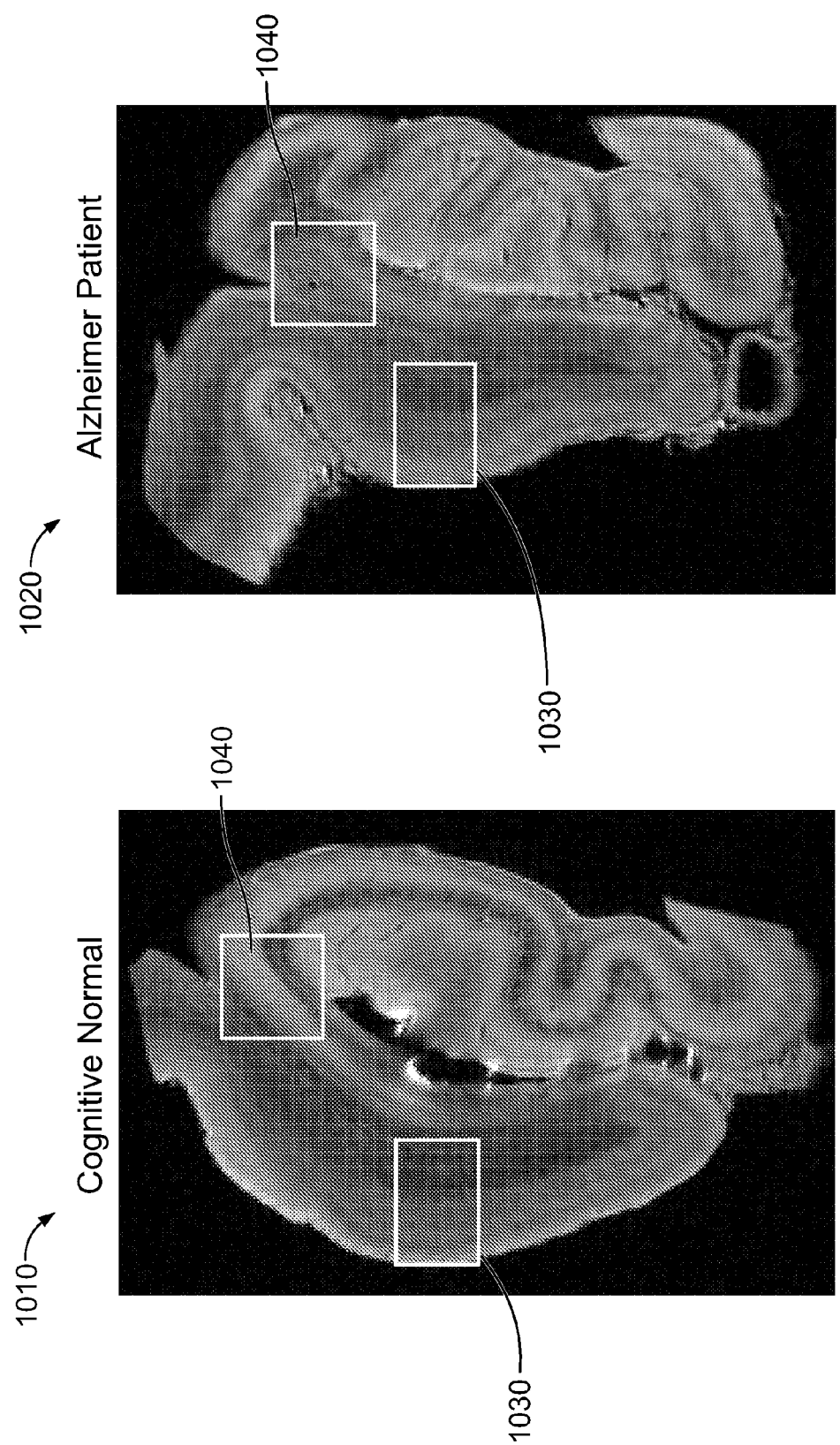
FIG. 10 illustrates T2-weighted reference images for a congnative normal subject and an AD subject.

An example of the use of FA in different brain regions to distinguish AD brains from cognitively normal brains is given in FIGS. 8-10. As shown in the figures, we have experimentally determined that FA is lower and directionality map is different in entorhinal cortex (a gray matter brain region), CA1 (a hippocampal subfield) and perforant path (hippocampal circuit) in the AD brain relative to the normal control brain. Based on this experimental finding, one or more embodiments of our invention provide that FA is a surrogate biomarker for dendritic density in the hippocampal region, and have potential to be used as a diagnostic method for Alzheimer's disease.

FIG. 8 shows DTI parametric maps of human brain tissue. Those in the left column 810 are from a cognitive normal subject, while those in the right column 820 are from an AD subject.

As shown in the Figure, the DTI parametric maps reveal decreased fractional anisotropy and directionality in the perforant path and CA1 in ex vivo tissue samples from a cognitive normal (left column 810) and AD patient (right column 820). FA maps of entorhinal cortex (EC; black outline) 830 and perforant path (PP; white outline) 840 reveal reduced FA values in the PP of the AD tissue as shown in 850 and 860. Note, as described above, that lower FA values indicate reduced preferred directionality.

Cylinder plots of EC and PP illustrating directionality in three dimensions 870, 880 reveal that through-plane directionality dominates in the PP of the normal tissue while a preferred directionality is lacking in the AD tissue.

FIG. 9 illustrates FA maps of hippocampal subfield CA1 for both a cognitive normal subject 910 and an AD subject 920. These diagrams reveal marginally reduced FA in AD tissue. Further, the 3-D directionality maps for the cognitive normal subject 930 and AD subject 940 indicate a reduction of in-plane directionality in the AD tissue which may indicate a reduction in dendritic density.

FIG. 10 illustrates T2-weighted reference images for a cognitive normal subject 1010 and an AD subject 1020. Additionally, the location of EC 1030 and PP and CA1 1040 in the cognitive normal and AD tissue is shown.

The FA values for the samples in FIGS. 8-10 are—for the AD sample: EC=0.198+/−0.088, PP=0.290+/−0.112, and CA1=0.227+/−0.082. For the Cognitive normal sample, the values are: EC=0.206+/−0.094, PP=0.445+/−0.171, and CA1=0.252+/−0.081. The DTI images in FIGS. 8-10 were acquired using a diffusion-weighted spin-echo imaging protocol: TR=3000 ms, TE=27 ms, $\Delta=14$ ms, $\delta=7$ ms, field of view=1.5 cm, and matrix size=256×256. Diffusion sensitizing gradients were applied along six directions with six b values, [200, 500, 1000, 1500, 2500 and 3500 s/mm$^2$] along each diffusion gradient direction.

Additionally, although AD may be the primary disease discussed above, any other neurodegenerative diseases or injury to the hippocampus may be diagnosed and/or evaluated.

Additionally, the system and method described above may be applied to other gray matter areas of the brain including but not limited to regions of the cerebral cortex, dentate gyrus, entorhinal cortex and subiculum.

Additionally, the system and method described above may be applied to AD diagnosis in humans, AD staging in humans, assess patient's response to therapy, assess drug efficacy in animal models of AD, neurodegenerative diseases or injury to the hippocampus.

Other applications of DTI-derived hippocampal fractional anisotropy as an index of the quantity of hippocampal dendrites could prove useful in a wide range of research and clinical areas related to normal and abnormal brain function such as brain development, schizophrenia and neurodegenerative diseases including spinocerebellar ataxia, Alzheimer's disease, prion diseases, and Sandhoff disease.

Additionally, we note that one or more embodiments of the present invention may be used to determine an increased probability of the presence of AD, rather than an explicit diagnosis. Additionally, one or more embodiments of the present invention may be employed to determine reduced dendritic volume.

Finally, we note that diffusion tensor imaging has only been used to study alterations in highly myelinated brain structures/regions where fractional anisotropy is high (FA has a range from 0 to 1, with 0 being the minimum and 1 being the maximum). Hippocampal subfields which have relatively moderate anisotropy (FA 0.25-0.50) have not been investigated using DTI. Furthermore, DTI is a novel area of MR imaging and thus far no studies have investigated the biological basis for anisotropy in any brain region.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features which come within the spirit and scope of the invention.

The invention claimed is:

1. A method for determining an increased likelihood that a subject has Alzheimer's Disease (AD) relative to a normal subject, said method including:
   imaging an area of the hippocampus of the brain of a subject to acquire a diffusion tensor age of said area;
   determining the Fractional Anisotropy (FA) from said diffusion tensor image;
   comparing said Fractional Anisotropy to normative data; and
   identifying an increased likelihood of the presence of AD relative to a normal subject when said FA is less than said normative data by a statistically significant amount, wherein said statistically significant amount has a p-value of less than 0.05.

2. The method of claim 1 wherein said diffusion tensor image is acquired using magnetic resonance imaging.

3. The method of claim 1 further including calculating the mean diffusitivity of said area.

4. The method of claim 3 wherein said mean diffusivity is also compared to normative data and an increased likelihood of the presence of AD relative to a normal subject is determined when said mean diffusivity is greater than said normative data.

5. The method of claim 1 further including calculating the eigenvectors for said area.

6. A method for identifying when a subject has reduced dendritic quantity in the hippocampus of the subject's brain, said method including:
   imaging an area of the hippocampus of the brain of a subject to acquire a diffusion tensor image of said area;
   determining the Fractional Anisotropy (FA) from said diffusion tensor image;
   comparing said Fractional Anisotropy to normative data; and
   identifying reduced dendritic quantity when said FA is less than said normative data by a statistically significant amount, wherein said statistically significant amount has a p-value of less than 0.05.

7. The method of claim 6 wherein said diffusion tensor image is acquired using magnetic resonance imaging.

8. The method of claim 6 further including calculating the mean diffusitivity of said area.

9. The method of claim 8 wherein said mean diffusivity is also compared to normative data and reduced dendritic quantity is determined when said mean diffusivity is greater than said normative data.

10. The method of claim 6 further including calculating the eigenvectors for said area.

* * * * *